United States Patent
Plumptre et al.

(10) Patent No.: US 10,471,217 B2
(45) Date of Patent: Nov. 12, 2019

(54) ASSEMBLY FOR A DRUG DELIVERY DEVICE COMPRISING A FEEDBACK FEATURE

(71) Applicant: Sanofi-Aventis Deutschland GmbH, Frankfurt am Main (DE)

(72) Inventors: David Aubrey Plumptre, Worcestershire (GB); Naceur Rekaya, Warwickshire (GB); Paul Richard Draper, Worcestershire (GB); Paul Griffin, Worcestershire (GB); Stephen Francis Gilmore, Bristol (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 707 days.

(21) Appl. No.: 14/771,178

(22) PCT Filed: Mar. 10, 2014

(86) PCT No.: PCT/EP2014/054526
§ 371 (c)(1),
(2) Date: Aug. 27, 2015

(87) PCT Pub. No.: WO2014/139914
PCT Pub. Date: Sep. 18, 2014

(65) Prior Publication Data
US 2016/0015899 A1    Jan. 21, 2016

(30) Foreign Application Priority Data
Mar. 13, 2013 (EP) .................... 13159047

(51) Int. Cl.
*A61M 5/315* (2006.01)

(52) U.S. Cl.
CPC ........ *A61M 5/3157* (2013.01); *A61M 5/3155* (2013.01); *A61M 2205/581* (2013.01); *A61M 2205/582* (2013.01)

(58) Field of Classification Search
CPC .......... A61M 5/31541; A61M 5/31551; A61M 5/3157; A61M 5/31585; A61M 5/5086;
(Continued)

(56) References Cited

U.S. PATENT DOCUMENTS

| | | |
|---|---|---|
| 533,575 A | 2/1895 | Wilkens |
| 4,865,591 A | 9/1989 | Sams |

(Continued)

FOREIGN PATENT DOCUMENTS

| | | |
|---|---|---|
| CA | 2138528 | 12/1998 |
| CA | 2359375 A1 | 7/2000 |

(Continued)

OTHER PUBLICATIONS

Communication Pursuant to Rule 114(2) EPC issued in European Patent Application No. 14708560.9 dated Dec. 1, 2016.
(Continued)

*Primary Examiner* — Theodore J Stigell
(74) *Attorney, Agent, or Firm* — Fish & Richardson P.C.

(57) ABSTRACT

An assembly for a drug delivery device is provided, the assembly comprising a feedback feature. The feedback feature is configured to indicate an end of the dispense operation to a user by giving an audible and/or tactile feedback.

16 Claims, 9 Drawing Sheets

(58) Field of Classification Search
CPC ...... A61M 2205/581; A61M 2205/582; A61M 5/3155
See application file for complete search history.

(56) References Cited

U.S. PATENT DOCUMENTS

| | | | |
|---|---|---|---|
| 5,092,842 | A | 3/1992 | Bechtold et al. |
| 5,226,895 | A | 7/1993 | Harris |
| 5,226,896 | A | 7/1993 | Harris |
| 5,279,586 | A | 1/1994 | Balkwill |
| 5,304,152 | A | 4/1994 | Sams |
| 5,320,609 | A | 6/1994 | Haber et al. |
| 5,378,233 | A | 1/1995 | Haber et al. |
| 5,383,865 | A | 1/1995 | Michel |
| 5,391,157 | A * | 2/1995 | Harris ............ A61M 5/31511 604/208 |
| 5,480,387 | A | 1/1996 | Gabriel et al. |
| 5,505,704 | A | 4/1996 | Pawelka et al. |
| 5,582,598 | A | 12/1996 | Chanoch |
| 5,626,566 | A | 5/1997 | Petersen et al. |
| 5,674,204 | A | 10/1997 | Chanoch |
| 5,688,251 | A | 11/1997 | Chanoch |
| 5,807,346 | A | 9/1998 | Frezza |
| 5,820,602 | A | 10/1998 | Kovelman et al. |
| 5,851,079 | A | 12/1998 | Horstman et al. |
| 5,921,966 | A | 7/1999 | Bendek et al. |
| 5,957,896 | A | 9/1999 | Bendek et al. |
| 5,961,495 | A | 10/1999 | Walters et al. |
| 6,004,297 | A | 12/1999 | Steenfeldt-Jensen et al. |
| 6,193,698 | B1 | 2/2001 | Kirchhofer et al. |
| 6,221,046 | B1 | 4/2001 | Burroughs et al. |
| 6,235,004 | B1 | 5/2001 | Steenfeldt-Jensen et al. |
| 6,248,095 | B1 | 6/2001 | Giambattista et al. |
| 6,562,006 | B1 | 5/2003 | Hjertman et al. |
| 6,613,023 | B2 | 9/2003 | Kirchhofer et al. |
| 6,699,224 | B2 | 3/2004 | Kirchhofer et al. |
| 6,899,698 | B2 | 5/2005 | Sams |
| 6,932,794 | B2 | 8/2005 | Giambattista et al. |
| 6,936,032 | B1 | 8/2005 | Bush, Jr. et al. |
| 7,169,132 | B2 | 1/2007 | Bendek et al. |
| 7,241,278 | B2 | 7/2007 | Moller |
| 7,427,275 | B2 | 9/2008 | DeRuntz et al. |
| 7,678,084 | B2 | 3/2010 | Judson et al. |
| 7,850,662 | B2 | 12/2010 | Veasey et al. |
| 8,186,223 | B2 | 5/2012 | Joung et al. |
| 2002/0052578 | A1 | 5/2002 | Moller |
| 2002/0120235 | A1 | 8/2002 | Enggaard |
| 2003/0050609 | A1 | 3/2003 | Sams |
| 2004/0059299 | A1 | 3/2004 | Moller |
| 2004/0097883 | A1 | 5/2004 | Roe |
| 2004/0210199 | A1 | 10/2004 | Atterbury et al. |
| 2004/0267207 | A1 | 12/2004 | Veasey et al. |
| 2005/0113765 | A1 | 5/2005 | Veasey et al. |
| 2006/0153693 | A1 | 7/2006 | Fiechter et al. |
| 2007/0016143 | A1 | 1/2007 | Miller et al. |
| 2009/0012479 | A1 * | 1/2009 | Moller ............... A61M 5/20 604/211 |
| 2009/0275916 | A1 | 11/2009 | Harms et al. |
| 2012/0310156 | A1 | 12/2012 | Karlsson et al. |

FOREIGN PATENT DOCUMENTS

| | | |
|---|---|---|
| CN | 1089510 | 7/1994 |
| CN | 101107032 | 1/2008 |
| EP | 0496141 A1 | 7/1992 |
| EP | 0897729 A2 | 2/1999 |
| EP | 0937471 A2 | 8/1999 |
| EP | 0937472 A2 | 8/1999 |
| EP | 0937476 A2 | 8/1999 |
| EP | 1776975 A2 | 4/2007 |
| EP | 1923083 A1 | 5/2008 |
| WO | 9307922 A1 | 4/1993 |
| WO | 9324160 A1 | 12/1993 |
| WO | 9938554 A1 | 8/1999 |
| WO | 0110484 A1 | 2/2001 |
| WO | 0230495 A2 | 4/2002 |
| WO | 02092153 A2 | 11/2002 |
| WO | 03080160 A1 | 10/2003 |
| WO | 2006084876 A1 | 8/2006 |
| WO | WO 2011/099918 | 8/2011 |
| WO | 2011123024 A1 | 10/2011 |
| WO | WO 2012/085584 | 6/2012 |
| WO | WO 2012/110577 | 8/2012 |

OTHER PUBLICATIONS

Extended European Search Report issued in European Patent Application No. 13159047.3, dated Oct. 1, 2013.
"Pen-injectors for medical use—Part 1: Pen-injectors—Requirements and test methods," International Standard, reference No. ISO 11608-1:2000(E), first edition Dec. 15, 2000, 32 pages.
International Preliminary Report on Patentability in International Application No. PCT/EP2014/054526, dated Sep. 15, 2015, 6 pages.
International Search Report and Written Opinion in Application No. PCT/EP2014/054526, dated Jun. 3, 2014, 11 pages.

* cited by examiner

ASSEMBLY FOR A DRUG DELIVERY DEVICE COMPRISING A FEEDBACK FEATURE

CROSS REFERENCE TO RELATED APPLICATIONS

The present application is a U.S. National Phase Application pursuant to 35 U.S.C. § 371 of International Application No. PCT/EP2014/054526 filed Mar. 10, 2014, which claims priority to European Patent Application No. 13159047.3 filed Mar. 13, 2013. The entire disclosure contents of these applications are herewith incorporated by reference into the present application.

FIELD OF INVENTION

The present disclosure relates to an assembly for a drug delivery device. The assembly comprises a feedback feature.

BACKGROUND

It is an object of the present invention to provide an assembly for a drug delivery device having improved properties.

An assembly for a drug delivery device is provided, the assembly comprising a feedback feature. The feedback feature is configured to indicate an end of a dispense operation to a user by giving an audible and/or tactile feedback. The audible feedback may be, for example, an audible click. The tactile feedback may be, for example, an impact on the skin of a user, in particular on a user's finger. For example, the tactile feedback may be a vibration of a part of the assembly. In particular, the feedback may be a well-defined signal. In particular, the feedback may indicate to a user that the actuator may be released and the device may be withdrawn from a user's skin.

The advantage of a feedback feature being configured to indicate the end of a dispense operation is that a clear indication is given to a user when a dispense operation has been completed. Thereby, the use of the drug delivery device may be simplified for a user. Furthermore, the dosing accuracy of a drug delivery device may be increased. In particular, it may be inhibited that a user interrupts a dispense operation, for example by withdrawing the drug delivery device from the skin, before a complete dose has been delivered. Furthermore, such a feedback provides an additional benefit for visually impaired users.

SUMMARY

According to one embodiment, the assembly comprises an actuator, which is configured to be operated by a user in order to dispense a dose. A feedback feature may create a feedback when the actuator reaches an end position at the end of a dispense operation. The end position of the actuator may be a most distal position of the actuator. The term "most distal position" may describe a position of a part of the assembly which is closest to a dispensing end of the drug delivery device. In particular, the actuator may be in its end position when it is fully depressed into the drug delivery device. The actuator may be configured as a button. According to one embodiment, the feedback feature may be an integral part of the actuator.

According to one embodiment, the assembly comprises a member which is configured to interact with the feedback feature. The member is configured to axially move when it does not interact with the feedback feature. For example, the member is configured to axially move during an initial phase of a dispense operation. The interaction of the axially moveable member with the feedback feature may cause a feedback. According to another embodiment, the member may be a driver. The driver may be a part of the assembly which is configured to drive a piston rod in order to dispense a dose of medication. In particular, the driver may be engaged with the piston rod. During a dispense operation, the driver may be moved towards a distal end of the device due to a movement of the actuator. According to a further embodiment, the member may be an indicator, for example a number sleeve. According to a further embodiment, the member may be a separate member, for example a sleeve member.

According to one embodiment, the member may axially move with respect to a housing of the drug delivery device between two stops at least during the setting of a dose. During the dispensing of a dose, in particular when the actuator approaches its end position, the member may be temporarily restrained between these two stops. Thereby, the member may be temporarily axially fixed. In particular, the member may be axially fixed when it interacts with the feedback feature, i. e. when the actuator contacts the feedback feature.

According to one embodiment, the feedback feature is configured to snap through when it is compressed above a certain load. Thereby, a feedback may be given to a user. In particular, the feedback feature is configured to snap through at the end of a dispense operation. In particular, the feedback feature is configured to snap through when the actuator reaches its end position. Initially during compression of the feedback feature, the stiffness of the feedback feature may remain fairly constant. At a certain point, the stiffness of the feedback feature may reduce significantly. Thereby, the force required to cause a further deflection of the feedback feature may decrease. This may cause the snap-through behaviour of the feedback feature.

According to one embodiment, the feedback feature may be configured to be compressed between two parts of the assembly. For example, the feedback feature may be compressed between the actuator and the axially moveable member. Alternatively, the feedback feature could be compressed between the housing and the driver.

According to one embodiment, the feedback feature may comprise the shape of a dome. In particular, the feedback feature may be configured as a snap dome. In particular, the feedback feature may comprise the shape of an arched disk.

According to one embodiment, the feedback feature comprises at least one recess. The recess may be, for example, a concave cut out. Due to the at least one recess, the feedback feature may comprise a sufficient flexibility. Thereby, the feedback feature may be configured to snap through when it is compressed above a certain load. In particular, the size and shape of the recess may influence the force which is necessary to cause the feedback feature to snap through.

According to one embodiment, the actuator interacts with the feedback feature. In particular, the actuator may interact with the feedback feature during a dispense operation. The feedback feature may be arranged between the actuator and another part of the drug delivery device. When the actuator approaches its end position during a dispense operation, the feedback feature may be clamped between the actuator and the other part. When the actuator is further moved towards the other part, the feedback feature may be compressed by the actuator. In particular, the force on the feedback feature increases when the actuator is further moved towards the other part. In particular, the actuator may exert a force on the feedback feature during a dispense operation. In an alternative embodiment, the feedback feature may be an integral part of the other part.

According to one embodiment, the feedback feature comprises a metal material. According to a further embodiment, the feedback feature may comprise a plastic material. Preferably, the feedback feature comprises a resilient material.

According to one embodiment, the feedback feature comprises an opening, wherein at least one element of the assembly extends through the opening. For example, the actuator may extend through the opening of the feedback feature. As a further example, the driver may extend through the opening of the feedback feature.

According to one embodiment, the feedback feature comprises a first feedback element and a second feedback element. The first feedback element may be configured to interact with the second feedback element. In particular, the first feedback element and the second feedback element may abut each other, in particular when the actuator approaches its end position. In particular, the second feedback element may exert a force on the first feedback element during the dispensing of a dose. Thereby, the first feedback element may be deflected by the second feedback element during a dispense operation. The first feedback element may be, for example, a resilient element. The second feedback element may be, for example, a rigid element. For example, the second feedback element may be a protrusion in a part of the assembly. In particular, the second feedback element may extend along the whole circumference of the part. For example, the second feedback element may be a protrusion which extends along an inner circumference of a body part of the assembly. When the first feedback element and the second feedback element interact with each other, an audible feedback may be created. The first feedback element may be an integral part of a part of the device. For example, the first feedback element may be an integral part of the actuator. Alternatively, the first feedback element may be an integral part of the indicator.

According to one embodiment, the feedback feature comprises at least one resilient arm. In particular, the first feedback element may comprise at least one resilient arm. Preferably, the feedback feature comprises two or more resilient arms. Preferably, the at least one resilient arm extends in a proximal direction. The proximal direction may be a direction away from the dispensing end of the device. In an alternative embodiment, the at least one resilient arm extends in a distal direction. According to one embodiment, the at least one resilient arm may stick out from an element of the assembly in a radial direction. During a dispense operation, the at least one resilient arm may be deflected, in particular in a radial direction. Preferably, the at least one resilient arm is integrally formed with a part of the assembly. Preferably, the at least one arm is attached to, in particular integrally moulded with an injection moulded part of the device.

According to one embodiment, the assembly comprises a rotation member which is configured to rotate during dispensing of a dose. The first feedback element of the feedback feature may be located at the rotation member. The rotation member may be, for example, an indicator, in particular a number sleeve. For example, the feedback feature may be a resilient arm which is attached to the rotation member. In particular, the feedback element may extend along a circumferential direction of the rotation member. Preferably, the feedback feature is configured to be deflected in a radial inward direction.

According to one embodiment, the feedback feature is configured to give a feedback to a user during the dispensing of a dose. In particular, the feedback may indicate that the dispensing is ongoing. As an example, a first feedback element may permanently interact with a second feedback element during a dispense operation. At the end of a dispense operation, the feedback may be increased.

According to one embodiment, the assembly comprises an enhancement feature. The enhancement feature may be configured to enhance a feedback signal. The enhancement feature may be, for example, a protrusion in one part of the assembly. According to one embodiment, the first feedback element is configured to interact with the enhancement feature at the end of the dispense operation. Preferably, the first feedback element does not interact with the enhancement feature prior to the end of the dispense operation. The enhancement feature may be configured to reinforce the interaction of the first feedback element with the second feedback element. The second feedback element may comprise a plurality of protrusions or splines. For example, the enhancement feature may increase the stiffness of the first feedback element. In particular, the enhancement feature may be in contact with the first feedback element at the end of a dispense operation. In particular, the enhancement feature may be in contact with a surface of the first feedback element which is faced towards a longitudinal axis of the device. Thereby, the enhancement feature may limit a deflection of the first feedback element, in particular in a radially inward direction.

According to one embodiment, the second feedback element is configured as a thread. For example, the second feedback element may comprise a thread in a body part of the assembly. The first feedback element may be a resilient arm, which is for example located at the rotation member and may extend along a circumference direction of the rotation member. During the dispensing of a dose, the first feedback element may interact with the thread of the second feedback element. In particular, the first feedback element may be preloaded due to the interaction with the thread of the second feedback element. For example, the first feedback element may be strained in an axial or radial direction. The second feedback element may further comprise a step. The step may be located at a distal end of the thread. The step may extend in an axial or radial direction. When the first feedback element reaches the step at the end of a dispense operation, the first feedback element may, due to its preload, drop of the step. Thereby, the first feedback element may hit the wall of the body part. Thereby, an audible feedback may be created.

Furthermore, a drug delivery device is provided, the drug delivery device comprising an assembly which is configured as previously described. In particular, the drug delivery device may comprise a feedback feature, which is configured to indicate an end of a dispense operation to a user by giving an audible and/or tactile feedback.

The drug delivery device may be an injection device. The drug delivery device may be a pen-type device. The drug delivery device may be a variable dose device such that a user can select the size of a dose. The drug delivery device may be configured for multiple dose applications. The medication may be delivered to a user by means of a needle. The device may be delivered to a user in a fully assembled condition ready for use. The drug delivery device may be a disposable device. The term "disposable" means that the drug delivery device cannot be reused after an available amount of medication has been delivered from the drug delivery device. The drug delivery device may be configured to deliver a liquid medication. The medication may be, for example, insulin.

The term "medication", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa http://en.wikipedia.org/wiki/Dalton_%28unit%29) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Further features, refinements and expediencies become apparent from the following description of the exemplary embodiments in connection with the figures.

DETAILED DESCRIPTION

Figure 1:
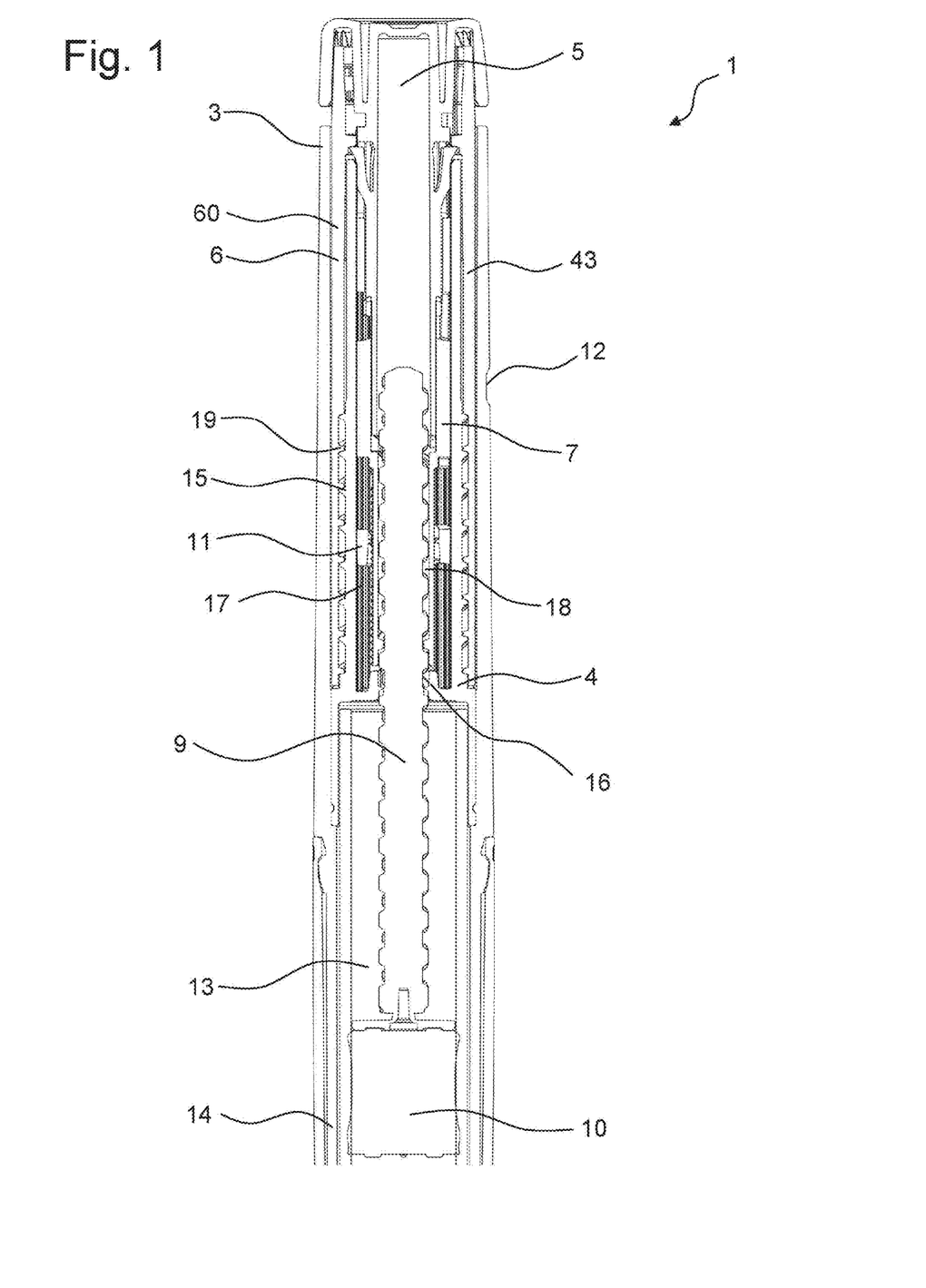
FIG. 1 shows a sectional view of a drug delivery device.

FIG. 1 shows a drug delivery device 1. In particular, the drug delivery device 1 is an injection device. The drug delivery device 1 is a variable dose device such that a user can select the size of a dose. The drug delivery device 1 is configured for multiple dose applications. The device can be delivered to a user in a fully assembled condition ready for use. The device has a low part count and is particularly attractive for cost-sensitive device applications.

The drug delivery device 1 comprises a housing 3, an inner body 4, an actuator 5, an indicator 6, a driver 7, a piston rod 9, a piston 10, a last dose stop 11, and a cartridge 13. A needle arrangement comprising a needle hub and a needle cover may be provided as additional components.

The housing 3 is a generally tubular element. A distal part of the housing 3 forms a cartridge holder 14 for receiving the cartridge 13.

The inner body 4 is a generally tubular element. The inner body 4 is received in the housing 3 and is permanently fixed therein to prevent any relative movement of the inner body 4 with respect to the housing 3. An external thread 15 is provided on the outer surface of the inner body 4. At its distal end, the inner body 4 comprises a further thread 16.

The actuator 5 is configured as a button. The actuator 5 is rotationally and axially moveable with respect to the housing 3 and the inner body 4. The actuator 5 is arranged at a proximal end of the drug delivery device 1. The actuator 5 is configured to be operated in order to dispense a dose of medication.

The indicator 6 is a generally tubular element. In particular, the indicator 6 is configured as a rotation member 43. In particular, the indicator 6 is configured to rotate with respect to the housing 3 during the setting and the dispensing of a dose. The indicator 6 is arranged concentrically around the inner body 4. In particular, the indicator 6 comprises an internal thread 19 engaging with the external thread 15 of the inner body 4. Thus, the indicator 6 is arranged between the inner body 4 and the housing 3. A series of numbers is provided, e.g. printed, on the outer surface of the indicator 6. The numbers are arranged on a helical line such that only one number or only a few numbers are visible through a window 12 of the housing 3. The numbers indicate the amount of a set dose. At the end of a dose dispense operation, the indicator 6 may have returned in its initial position, thereby indicating the end of a dispense operation to a user.

The piston rod 9 is configured as a lead screw. In particular, the piston rod 9 comprises two counter-handed threads which overlap each other. One of the threads of the piston rod 9 engages with the inner thread 16 of the inner body 4.

The driver 7 is a generally tubular element. An inner surface of the driver 7 has an inner thread 18 engaging with one of the external threads of the piston rod 9. The driver 7 is at least partly located within the inner body 4. A distal region of the driver 7 has an external thread 17. The driver 7 is configured to rotate and axially move with respect to the housing 3 during the setting of a dose. During the dispensing of a dose, the driver 7 is axially moveable and rotationally fixed with respect to the housing 3.

The last dose stop 11 is provided between the inner body 4 and the driver 7. An internal thread of the last dose stop 11 engages with the external thread 17 of the driver 7. The last dose stop 11 is configured to inhibit the setting of a dose which is larger than an amount of medication remaining in the cartridge 13. This is achieved by the last dose stop 11 abutting an abutment feature of the driver 7 when a dose is set which corresponds to an amount of medication remaining in the cartridge 13. The last dose stop 11 is configured as a nut.

In order to set a dose, the actuator 5 is rotated by a user. During the setting of a dose, the indicator 6 and the driver 7 are rotationally fixed with respect to the actuator 5. Thereby, the actuator 5, the indicator 6 and the driver 7 are rotated out of the housing 3. Thereby, the driver 7 is rotated along the piston rod 9 in a proximal direction, while the piston rod 9 is axially and rotationally fixed with respect to the housing 3 during the setting of a dose. The indicator 6 is rotated along the thread 15 of the inner body 4.

In order to dispense a dose, the actuator 5 is operated by a user. In particular, the actuator 5 is pushed in a direction towards a dispensing end of the device. During the dispensing of a dose, the actuator 5 and the driver 7 are rotationally fixed with respect to each other. The indicator 6 may rotate with respect to the actuator 5 and the driver 6 during the dispensing of a dose. Thereby, the indicator 6 may rotate back to its initial position and indicate the end of the dispense operation to a user. When the actuator 5 is operated, the driver 7 is also moved in a direction towards a dispensing end of the device. Thereby, the piston rod 9 is axially moved in a distal direction in order to dispense a dose of medication. In particular, the piston rod 9 is configured to rotate and axially move during the dispensing of a dose. When the actuator 5 has been operated and reached an end position, a feedback is given to a user. In particular, the feedback may indicate the end of a dispense operation. The end position of the actuator 5 may be its most distal position. In particular, the actuator 5 is in its end position when it is fully depressed.

In FIGS. 2 to 12B, different embodiments of a feedback feature are shown, which may indicate an end of a dispense operation to a user. In particular, FIGS. 2 to 5 and 7 to 12B show different assemblies 60 for a drug delivery device 1 comprising different embodiments of a feedback feature 2. The embodiments are illustrated in the context of a drug delivery device 1 as shown in FIG. 1, but are not limited thereto. In particular, the feedback feature 2 may also be used in a reusable device or in a device having a different drive mechanism.

The feedback may be an audible or tactile signal at the end of a dispense operation. This may improve the ease of use and the dose accuracy for a user, in particular for a visually impaired user. Furthermore, the signal can be used to indicate the start of a dwell period. At the end of a dispense operation, i. e. after a user has operated the actuator 5, the dispensing of the full amount of a set dose may be delayed due to a slight deformation of the piston 10. The dwell period is the time between the moment when the actuator 5 has reached its end position and the moment when the full amount of a dose has been dispensed. In particular, the dwell period may be the time the piston 10 needs after an operation of the actuator 5 to relax to its undeformed state.

Figure 2:
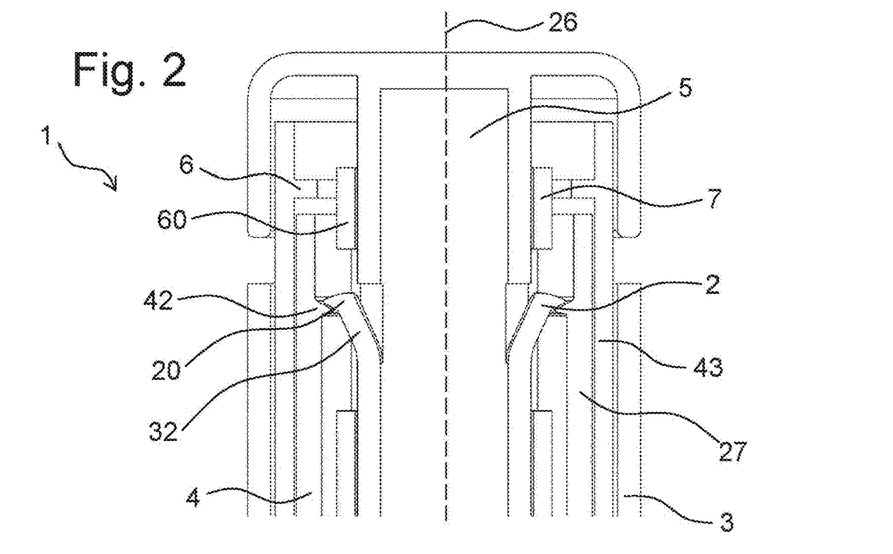
FIG. 2 shows a proximal part of a drug delivery device.

FIG. 2 shows a section through a proximal part of a drug delivery device 1 according to FIG. 1 comprising a feedback feature 2. A first feedback element 32 of the feedback feature 2 is arranged at the actuator 5. The first feedback element 32 is integrally formed with the actuator 5. In particular, the actuator 5 may be an injection-moulded part, wherein the first feedback element 32 may be integrally moulded with the actuator 5. The first feedback element 32 comprises at least one, in particular two resilient arms 20, which stick out from the actuator 5 in a radial direction. In particular, the resilient arms 20 stick out in a direction away from a longitudinal axis 26 of the drug delivery device 1. The resilient arms 20 may be configured as a snap feature. In particular, the resilient arms 20 are configured to snap over a second feedback element 42 of the feedback feature 2. The resilient arms 20 extend in a proximal direction. In particular, each resilient arm 20 has one connection point with a main body of the actuator 5 and one free end. The free end is faced towards a proximal end of the device 1. The driver 7 comprises a cavity 27, wherein the feedback feature 2, in particular the resilient arms 20, extend through the cavity 27.

When the actuator 5 is actuated by a user, the actuator 5 and thereby the first feedback element 32 is moved in a direction towards a distal end of the device 1. During the movement of the actuator 5 towards the distal end of the device 1, the first feedback element 32 interacts with the second feedback element 42. The second feedback element 42 is configured as a protrusion. The second feedback element 42 is located at the inner body 4. The second feedback element 42 may be configured as a full ring detent feature. This is beneficial in the case that the actuator 5 may have any rotational alignment relative to the inner body 4.

During the movement of the actuator 5 towards the distal end of the device 1, the first feedback element 32 is deflected in a radial direction towards the longitudinal axis 26 of the device 1, i.e. radially inwards. In particular, the resilient arms 20 are deflected by the second feedback element 42. When the actuator 5 has reached its end position, in particular at the end of a dispense operation, the resilient arms 20 lose contact with the second feedback element 42 and snap back in a direction away from the longitudinal axis 26 of the device 1. Thereby, an audible and/or tactile feedback is created. In an alternative embodiment, the first feedback element 32, in particular the resilient arms 20, may be located on the inner body 4, and the second feedback element 42 may be located on the actuator 5.

During the setting of a dose, when the actuator 5 is moved in a direction away from the dispensing end of the device 1, the resilient arms 20 are again deflected radially inwards by the second feedback element 32. Thereby, the resilient arms 20 may slide back over the second feedback element 42 such that they are again in a proximal position relative to the second feedback element 42.

Figure 3:
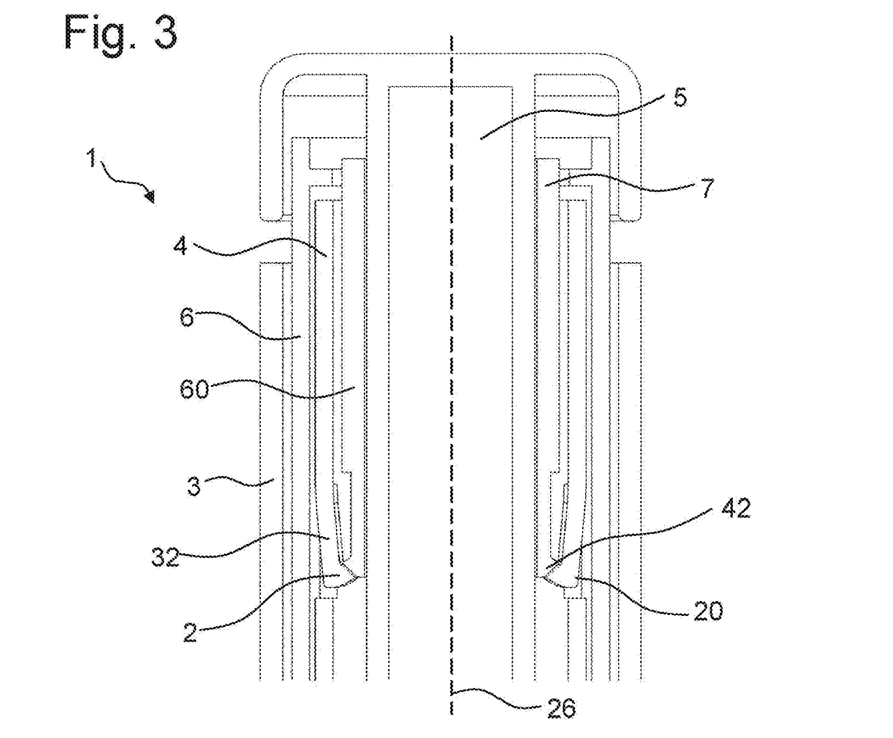
FIG. 3 shows a proximal part of a further embodiment of a drug delivery device.

FIG. 3 shows a section through a proximal part of a further embodiment of a drug delivery device 1 with a feedback feature 2. The feedback feature 2 comprises a first feedback element 32 and a second feedback element 42. The first feedback element 32 is located at the inner body 4. The first feedback element 32 comprises two resilient arms 20. The resilient arms 20 stick out from the inner body 4 in a radial direction towards the longitudinal axis 26 of the drug delivery device 1. The resilient arms 20 extend in a proximal direction. The first feedback element 32, in particular the resilient arms 20, interact with the second feedback element 42. The second feedback element 42 is located at the driver 7. In particular, the second feedback element 32 is configured as a protrusion on the driver 7. Since the driver 7 can have any rotational alignment to the inner body 4, the second feedback element 42 may be configured as a full ring detent feature.

The operating principle is similar to the embodiment described in FIG. 2. During the movement of the actuator 5 towards a distal end of the device, the driver 7 is also moved towards the distal end of the device. Thereby, the first feedback element 32, in particular the resilient arms 20, are deflected in a radial direction away from the longitudinal axis 26 of the device 1, i. e. radially outwards. When the actuator 5 has traveled its full distance, in particular at the end of a dispense operation, the first feedback element 32, in particular the resilient arms 20, lose contact with the second feedback element 42 of the driver and snap back in a direction towards the longitudinal axis 26 of the device. Thereby, an audible and/or tactile feedback is created. In an alternative embodiment, the first feedback element 32, in particular the resilient arms 20, may be located at the driver 7, and the second feedback element 42 may be located at the inner body 4.

During the setting of a dose, when the actuator 5 is moved in a direction away from the dispensing end of the device 1, the resilient arms 20 are again deflected radially outwards by the second feedback element 42. Thereby, the resilient arms 20 may slide back over the second feedback element 42 such that they are again in a distal position relative to the second feedback element 42.

Figure 4A:
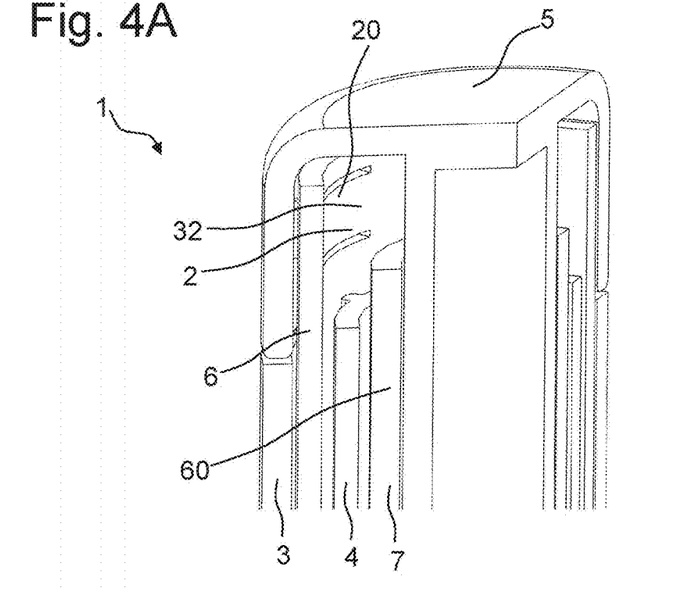
FIGS. 4A and 4B show a proximal part of a further embodiment of a drug delivery device.
Figure 4B:
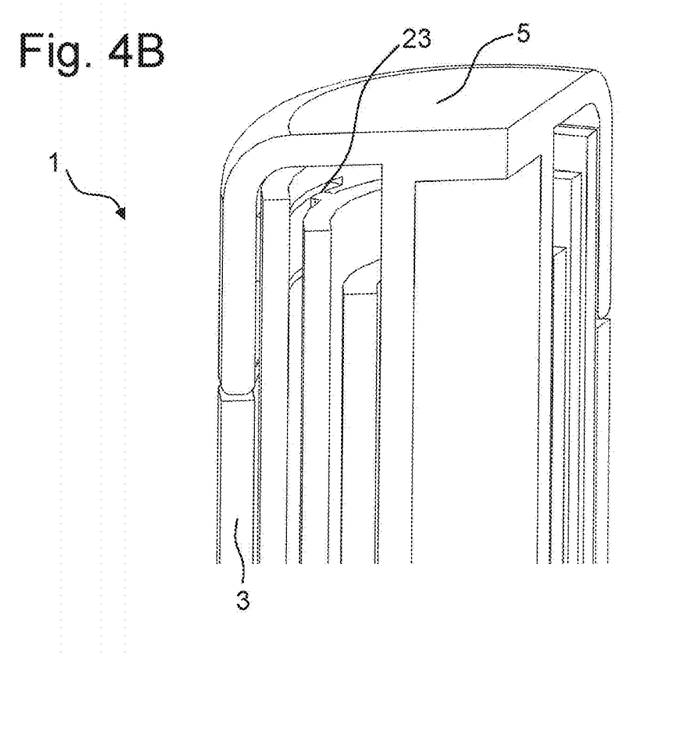

FIGS. 4A and 4B show a section through a proximal part of a further embodiment of a drug delivery device 1 comprising a feedback feature 2. The feedback feature 2 comprises a first feedback element 32 and a second feedback element 42.

The first feedback element 32 is arranged at the indicator 6. The first feedback element 32 may be an integral part of the indicator 6. In particular, the first feedback element 32 extends along a circumferential direction of the indicator 6. In particular, the first feedback element 32 comprises a resilient arm 20. When the indicator 6 rotates relative to the actuator 5 and the inner body 4 during the dispensing of a dose, the first feedback element 32, in particular the resilient arm 20, interacts with a second feedback element (not shown) inside the actuator 5 to provide an audible click with each unit dispensed. The second feedback element inside the actuator 5 may comprise, for example, teeth or splines. At the inner body 4, an enhancement feature 23 is arranged. The enhancement feature 23 is configured to interact with the first feedback element 32.

FIG. 4B shows the interaction of the first feedback element 32 and the enhancement feature 23. The enhancement feature 23 interacts with the first feedback element 32 at the end of a dispense operation. Due to the interaction of the first feedback element 32 and the enhancement feature 23, support is provided to the first feedback element 32 at least when the final unit of a dose is injected. In particular, the enhancement feature 23 interacts with the first feedback element 32 such that a deflection of the first feedback element 32 in a radially inward direction is limited. Thereby, the stiffness of the first feedback element 32 in particular of the resilient arm 20, is increased. Thereby, the interaction of the first feedback element 32 and the second feedback element inside the actuator 5 is increased. Thereby, a louder or a noticeably different click is produced, signalling to the user the end of a dispense operation.

Figure 5:
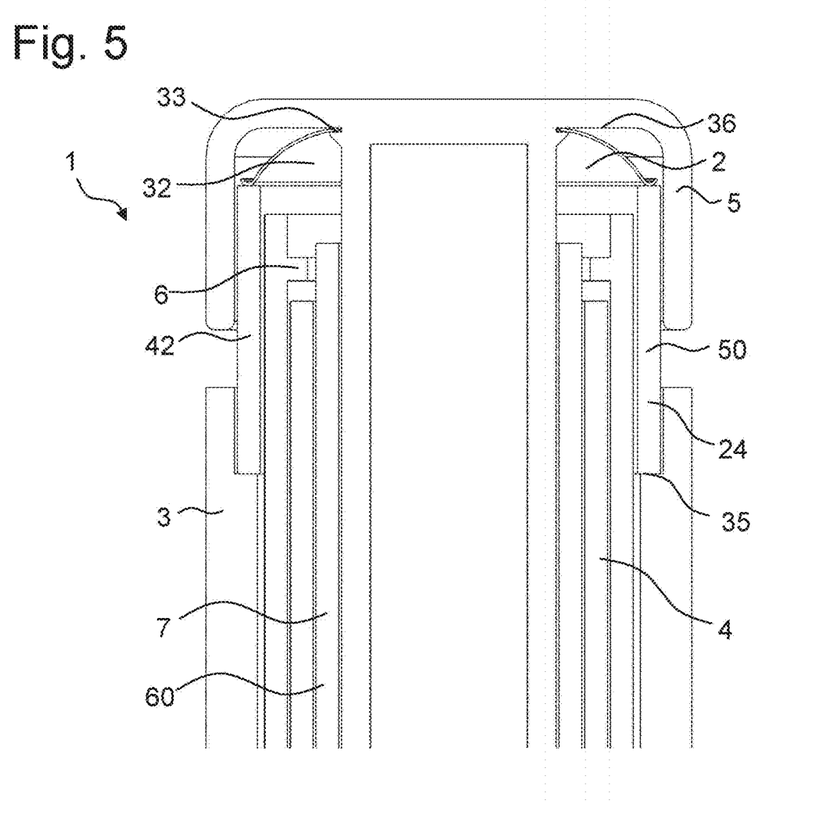
FIG. 5 shows a proximal part of a further embodiment of a drug delivery device.

FIG. 5 shows a further embodiment of a drug delivery device 1 comprising a feedback feature 2. The feedback feature 2 is configured as a snap feature. In particular, the feedback feature 2 is configured as a snap dome. The feedback feature 2 comprises or consists of a metal material. The feedback feature 2 comprises an opening 33, wherein the actuator 5 extends through the opening.

Figure 6A:
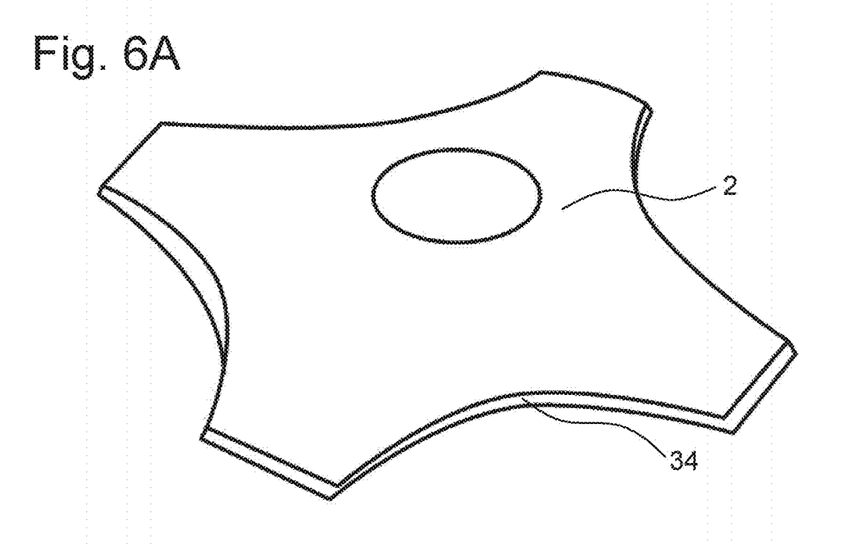
FIG. 6A shows a schematic view of a feedback feature.

A feedback feature 2 being configured as a snap dome is shown in FIG. 6A. In particular, the feedback feature 2 is configured as an arched disc. Furthermore, the feedback feature 2 comprises at least one recess 34. The recess 34 is configured as a concave cavity. In particular, the feedback feature 2 comprises four recesses 34. Due to the cavities, the snap dome possesses a sufficient flexibility. The feedback feature 2 is configured to snap through when it is compressed above a certain load. Thereby, the feedback feature 2 creates an audible click and/or a tactile feedback at the end of a dispense operation.

Figure 6B:
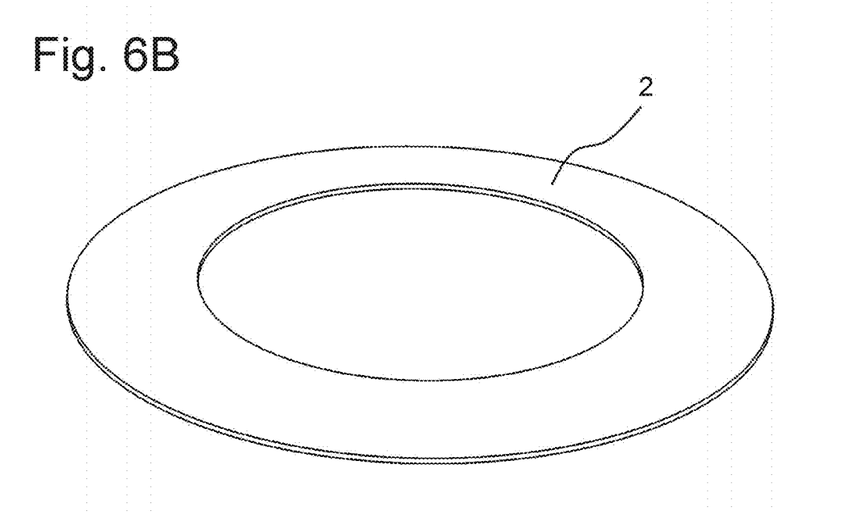
FIG. 6B shows a schematic view of a further feedback feature.

In an alternative embodiment as shown in FIG. 6B, the feedback feature 2 is configured without any recess. Thereby, the feedback feature 2 may comprise a high stiffness. Thereby, the feedback signal may be more distinct. In particular, the feedback feature 2 is configured as an arched ring. In particular, the feedback feature 2 comprises an opening.

As illustrated in FIG. 5, the feedback feature 2 is operated by an axially moveable member 50. In particular, the axially moveable member 50 is a sleeve member 24 which is arranged between the actuator 5 and the indicator 6. The sleeve member 24 can move axially relative to the actuator 5 between two stops 35, 36 when it does not interact with the feedback feature 2. The feedback feature 2 pushes apart the actuator 5 and the sleeve member 24 to preload the sleeve member 24 against one of these stops 35, 36. In particular, one stop 35 is provided by the housing 3 and the other stop 36 is provided by the actuator 5. When the actuator 5 approaches its end position, the sleeve member 24 contacts the stop 35 at the housing 3. When the actuator 5 is further moved towards its end position, the feedback feature 2 is compressed. Thereby, the feedback feature 2 is caused to snap, thereby creating an audible click. In particular, a clear audible and tactile feedback is provided for a user at the end of a dispense operation.

When the load which is exerted on the feedback feature 2 by the sleeve member 24 is released during the setting of a dose, the feedback feature 2 snaps back into its uncompressed shape. Thereby, the feedback feature 2 may push the actuator 5 to an extended position.

Figure 7:
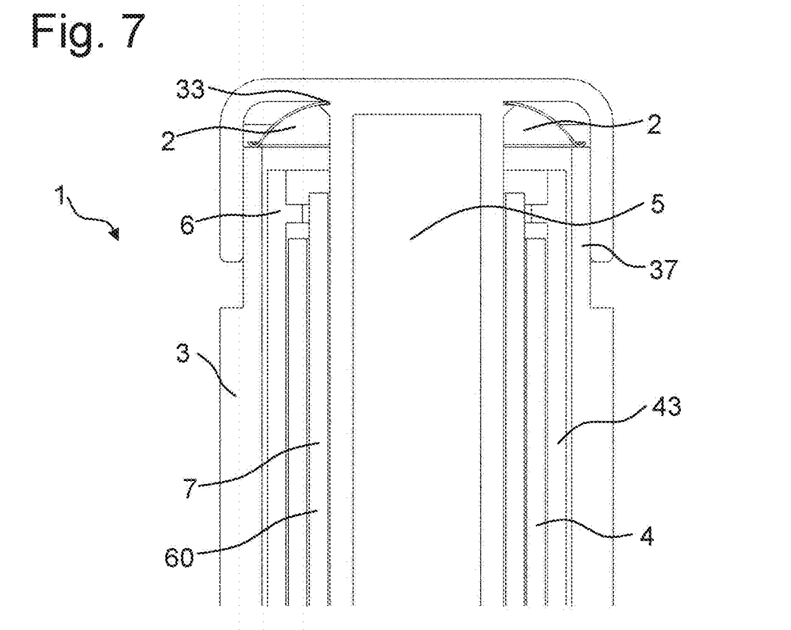
FIG. 7 shows a proximal part of a further embodiment of a drug delivery device.

FIG. 7 shows a section through a proximal part of a further embodiment of a drug delivery device 1 comprising a feedback feature 2. The embodiment shown in FIG. 7 is similar to the embodiment shown in FIG. 5, apart from that the embodiment shown in FIG. 7 does not comprise a sleeve member 24. The feedback feature 2 directly interacts with the actuator 5 and the housing 3. In particular, the housing 3 comprises a collar 37. The collar 37 is configured to interact with the feedback feature 2. In particular, the feedback feature 2 is compressed between the collar 37 of the housing 3 and the actuator 5 when the actuator 5 approaches the housing 3 during the dispensing of a dose.

Figure 8:
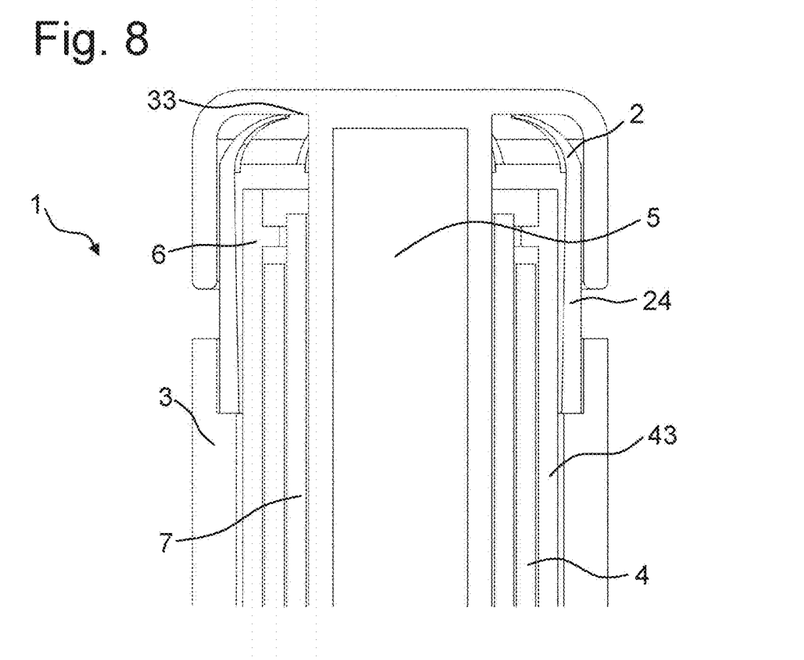
FIG. 8 shows a proximal part of a further embodiment of a drug delivery device.

FIG. 8 shows a proximal part of a different embodiment of a drug delivery device 1 comprising a feedback feature 2. The embodiment shown in FIG. 8 is similar to the embodiment shown in FIG. 5, apart from that the feedback feature 2 is integrated into the axially moveable member 50, which is configured as a sleeve member 24. In particular, the sleeve member 24 may be an injection-moulded part, and the feedback feature 2 may be integrally moulded with the sleeve member 24. The feedback feature 2 may be configured as a plastic dome or a series of resilient arms. The resilient arms may be arched, such that they form a dome with slots. The operating principle is the same as in the embodiment shown in FIG. 5, with the feedback feature 2 snapping through, thereby creating an audible and/or tactile feedback for a user at the end of a dispense operation.

Figure 9:
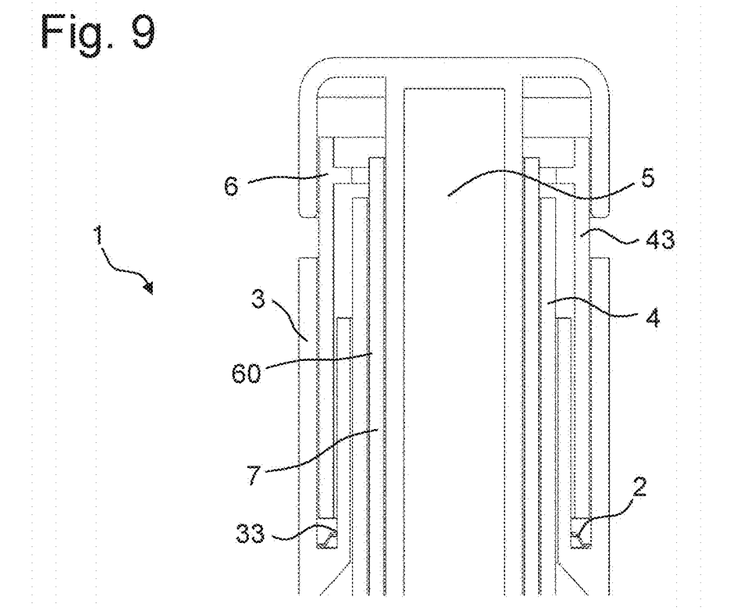
FIG. 9 shows a proximal part of a further embodiment of a drug delivery device.

FIG. 9 shows a section through a proximal part of a further embodiment of the drug delivery device 1 comprising a feedback feature 2. The feedback feature 2 is arranged between the indicator 6 and the housing 3. In particular, the feedback feature 2 is positioned inside a cavity in the housing 3. The feedback feature 2 is configured as a snap dome with a relatively large diameter. The actuator 5, the driver 7, the inner body 4 and a part of the housing 3 extend through the opening.

When the indicator 6 approaches its end-of-dispense position, it makes contact with the feedback feature 2 and compresses the feedback feature 2, thereby causing it to undergo snap-through buckling. Thereby, an audible and/or tactile feedback is created to indicate the end of a dispense operation to a user.

Figure 10:
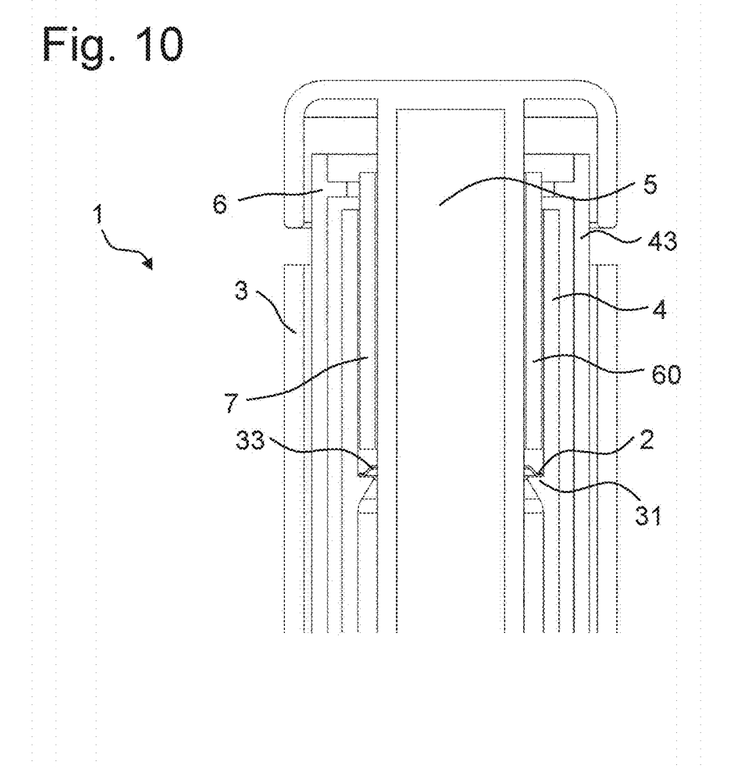
FIG. 10 shows a proximal part of a further embodiment of a drug delivery device.

FIG. 10 shows a section through a proximal part of a further embodiment of a drug delivery device 1 comprising a feedback feature 2. The embodiment shown in FIG. 10 is similar to the embodiment shown in FIG. 9, apart from that the feedback feature 2 is arranged between the driver 7 and the inner body 4. The feedback feature 2 is arranged on a protrusion 31 of the inner body 4. When the driver 7 approaches its end-of-dispense position, it makes contact with the feedback feature 2 and compresses the feedback feature 2, thereby causing the feedback feature 2 to snap through. Thereby, an audible and/or tactile feedback is created, indicating the end of a dispense operation to a user.

Figure 11A:
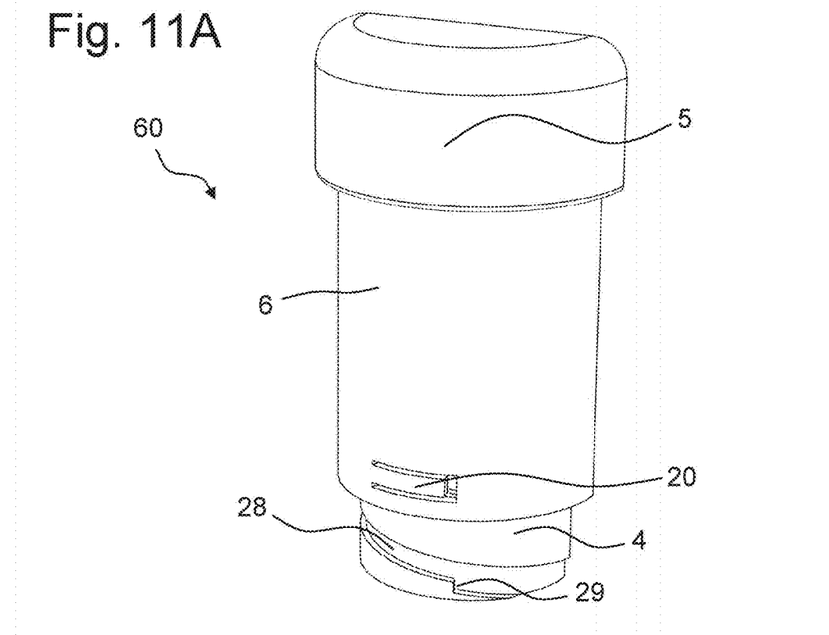
FIG. 11A shows a schematic view of an assembly for a drug delivery device.
Figure 11B:
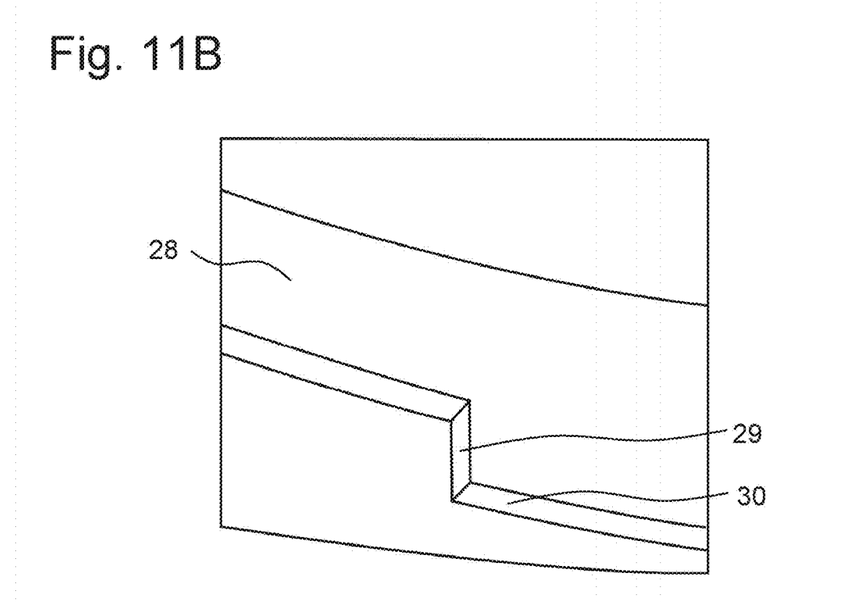
FIG. 11B shows a section of an inner body of the assembly of FIG. 11A.

FIG. 11A shows the actuator 5, the indicator 6 and the inner body 4 of a drug delivery device 1 according to FIG. 1. The indicator 6 comprises a first feedback element 32, which is configured as a resilient arm 20. The first feedback element 32 extends along a circumferential direction of the indicator 6. The feedback feature 2, in particular the resilient arm 20, is arranged at a distal end of the indicator 6. A thread 28, which is configured to interact with the feedback feature 2, is formed on the inner body 4. A second feedback element 42 is formed in the thread 28. The second feedback element 42 is configured as a step 29 in the thread 28. At the end of a dispense operation, the resilient arm 20 passes over the step 29. When the resilient arm 20 passes over the step 29, it is preloaded in an axial direction. In particular, the resilient arm 20 is preloaded in a direction towards the proximal end of the device 1. This preload could be retained throughout the travel of the indicator 6. Alternatively, the thread pitch could alter such that the resilient arm 20 is preloaded near to the end of the dispense operation. As a result of this preload, the resilient arm 20 accelerates rapidly as it drops off the step 29. Thereby, the resilient arm 20 strikes the thread wall 30 near the bottom of the step 29. Thereby, and audible and/or tactile signal is created, which indicates the end of a dispense operation to a user. FIG. 11B shows a section of the inner body 4 showing the step 29 in the thread 28 in more detail.

Figure 12A:
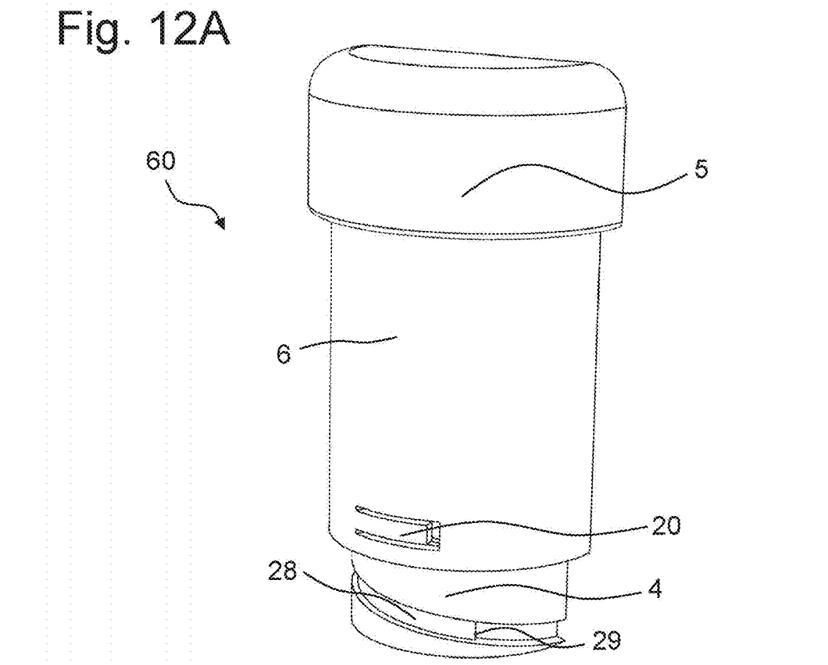
FIG. 12A shows a schematic view of a further assembly for a drug delivery device.
Figure 12B:
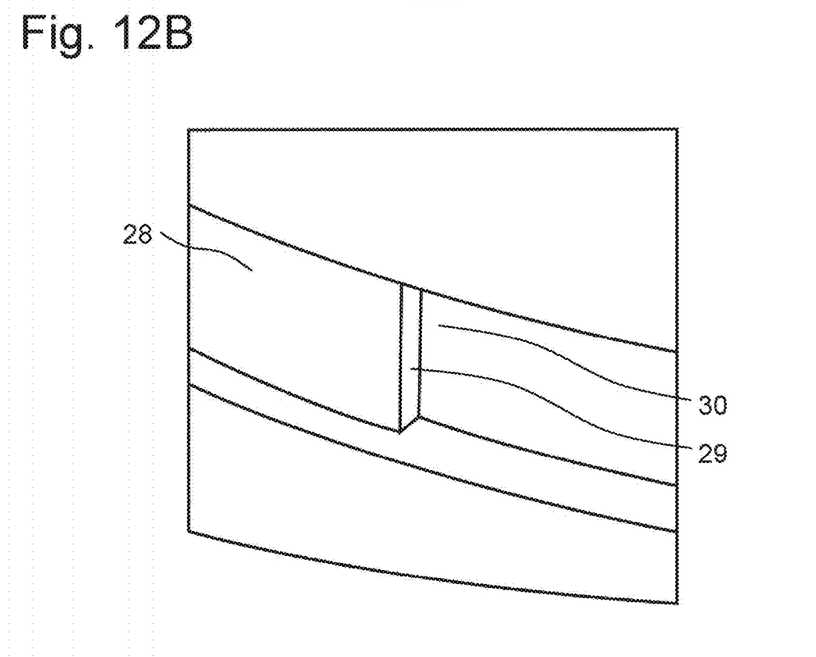
FIG. 12B shows a section of an inner body of the assembly of FIG. 12A.

FIG. 12A shows the actuator 5, the indicator 6 and the inner body 4 of a drug delivery device 1 according to FIG. 1. The embodiment according to FIG. 12A is similar to the embodiment shown in FIG. 11A. The indicator 6 also comprises a first feedback element 32 comprising a resilient arm 20, which is configured to interact with a thread 28 formed on the inner body 4. In the embodiment shown in FIG. 12A, the resilient arm 20 is configured to be preloaded radially outwards by the floor of the thread 28. This preload could be retained throughout the travel of the indicator 6. Alternatively, the preload could be generated when the indicator 6 is approaching its end of dispense position. In particular, the floor of the thread 28 could be raised such that the resilient arm 20 is preloaded near the end of the dispense operation. In the embodiment shown in FIG. 12A, the second feedback element 42, or the step 29, respectively, is radial, causing the resilient arm 20 to accelerate radially inwards and hit the inner body 4. Thereby, an audible and/or tactile signal is created, which indicates the end of a dispense operation to a user. FIG. 12B shows a section of the inner body 4 showing the step 29 in the thread 28 in more detail.

The invention claimed is:

1. An assembly for a drug delivery device, the assembly comprising:
   a feedback feature being configured to indicate an end of a dispense operation to a user by giving a feedback, the feedback being an audible and/or tactile feedback,
   an actuator which is configured to be operated in order to dispense a dose, wherein the feedback feature creates the feedback when the actuator reaches an end position at the end of the dispense operation,
   a rotation member which is configured to rotate during the dispense of the dose, wherein the feedback feature comprises a first feedback element which is located at the rotation member, and
   a second feedback element, wherein the first feedback element is configured to interact with the second feedback element, wherein the first feedback element is configured to interact with an enhancement feature at the end of the dispense operation, and wherein the enhancement feature is configured to reinforce an interaction of the first feedback element with the second feedback element.

2. The assembly according to claim 1, wherein the first feedback element extends along a circumferential direction of the rotation member.

3. The assembly according to claim 1, wherein configurations of the enhancement feature to reinforce the interaction of the first feedback element with the second feedback element comprise configurations to increase a magnitude of the feedback at the end of the dispense operation.

4. The assembly according to claim 1, wherein the rotation member comprises an indicator to indicate an amount of a set dose.

5. The assembly according to claim 1, wherein the second feedback element comprises teeth or splines.

6. The assembly according to claim 1, wherein the second feedback element is positioned inside the actuator.

7. The assembly according to claim 1, wherein the enhancement feature is arranged at an inner body of the assembly.

8. The assembly according to claim 1, wherein the enhancement feature is configured to interact with the first feedback element such that a deflection of the first feedback element is limited in a radially inward direction.

9. The assembly according to claim 1, wherein the feedback comprises an audible feedback, and configurations of the enhancement feature to reinforce the interaction of the first feedback element with the second feedback element comprise configurations to increase a loudness of the audible feedback.

10. A drug delivery device comprising an assembly according to claim 1.

11. An assembly for a drug delivery device, the assembly comprising:
    a feedback feature being configured to indicate an end of a dispense operation to a user by giving a feedback, the feedback being an audible and/or tactile feedback,
    an actuator which is configured to be operated in order to dispense a dose, wherein the feedback feature creates the feedback when the actuator reaches an end position at the end of the dispense operation,
    a rotation member which is configured to rotate during the dispense of a dose, wherein the feedback feature comprises a first feedback element comprising at least one resilient arm and which is located at the rotation member, and
    a second feedback element comprising a protrusion, wherein the first feedback element is configured to interact with the second feedback element, wherein the first feedback element is configured to interact with an enhancement feature comprising a protrusion at the end of the dispense operation, and wherein the protrusion of the enhancement feature is configured to reinforce an interaction of the at least one resilient arm of the first feedback element with the protrusion of the second feedback element.

12. The assembly according to claim 11, wherein the first feedback element is integral to the rotation member.

13. The assembly according to claim 11, wherein the first feedback element extends in a circumferential direction of the rotation member.

14. The assembly according to claim 11, wherein the rotation member comprises an indicator to indicate an amount of a set dose.

15. The assembly according to claim 11, wherein the protrusion of the second feedback element comprises teeth or splines.

16. The assembly according to claim 11, wherein the second feedback element is positioned inside the actuator.

* * * * *